(12) United States Patent
Longmire et al.

(10) Patent No.: US 11,631,041 B2
(45) Date of Patent: Apr. 18, 2023

(54) METHODS AND SYSTEMS FOR CREATING AND MANAGING A RESEARCH STUDY AND DEPLOYING VIA MOBILE AND WEB UTILIZING A RESEARCH MODULE

(71) Applicant: Medable Inc., Palo Alto, CA (US)

(72) Inventors: Michelle Rae Longmire, Palo Alto, CA (US); Ingrid Oakley-Girvan, Palo Alto, CA (US); Timothy Robert Smith, Palo Alto, CA (US); James Marcel Sas, Palo Alto, CA (US); Niraj Patel, Palo Alto, CA (US); Guillermo Biset, Palo Alto, CA (US); Fernando Waigandt, Palo Alto, CA (US); Matthew Lean, Palo Alto, CA (US); Analia Gigena, Palo Alto, CA (US)

(73) Assignee: Medable Inc., Palo Alto, CA (US)

( * ) Notice: Subject to any disclaimer, the term of this patent is extended or adjusted under 35 U.S.C. 154(b) by 0 days.

(21) Appl. No.: 16/304,283

(22) PCT Filed: May 24, 2017

(86) PCT No.: PCT/US2017/034335
§ 371 (c)(1),
(2) Date: Nov. 24, 2018

(87) PCT Pub. No.: WO2017/205544
PCT Pub. Date: Nov. 30, 2017

(65) Prior Publication Data
US 2019/0096511 A1  Mar. 28, 2019

Related U.S. Application Data

(60) Provisional application No. 62/341,062, filed on May 24, 2016.

(51) Int. Cl.
G06Q 10/06 (2012.01)
G06Q 10/0639 (2023.01)
(Continued)

(52) U.S. Cl.
CPC ........... *G06Q 10/0639* (2013.01); *G06F 7/00* (2013.01); *G06F 16/33* (2019.01); *G06F 40/174* (2020.01); *G06Q 40/08* (2013.01); *G16H 10/20* (2018.01)

(58) Field of Classification Search
CPC .......... G06F 16/33; G06F 40/174; G06F 7/00; G16H 10/20; G06Q 10/0639; G06Q 50/22
(Continued)

(56) References Cited

U.S. PATENT DOCUMENTS

| 7,756,829 B2 * | 7/2010 | Bhanote ................ G06Q 30/02 707/634 |
| 2002/0007303 A1 * | 1/2002 | Brookler ............... G06Q 30/02 705/7.32 |

(Continued)

FOREIGN PATENT DOCUMENTS

WO   WO-2016170368 A1 *  10/2016   ......... G06F 17/2705

OTHER PUBLICATIONS

McAlindon, Tim, Margaret Formica, Karim Kabbara, Michael LaValley, and Melissa Lehmer. "Conducting clinical trials over the internet: feasibility study." BMJ 327, No. 7413 (2003): 484-487. (Year: 2003).*

(Continued)

*Primary Examiner* — Frank D Mills
(74) *Attorney, Agent, or Firm* — Cesari and McKenna, LLP

(57) ABSTRACT

Systems and methods as disclosed herein are provided for generating a research study application. A request to gener-
(Continued)

ate a research study is received from a user. A plurality of task generation options are presented on a graphical user interface of an electronic device. The plurality of task generation options are selected from the group consisting of a consent survey, an eligibility survey, a medical history survey, and a medical tracking survey. Input regarding the plurality of task generation options is received from the user. Additionally, a research study application is generated based on information received from the user.

20 Claims, 30 Drawing Sheets

(51) Int. Cl.
*G06F 7/00* (2006.01)
*G06F 40/174* (2020.01)
*G06Q 40/08* (2012.01)
*G16H 10/20* (2018.01)
*G06F 16/33* (2019.01)

(58) Field of Classification Search
USPC .................................................... 715/222
See application file for complete search history.

(56) References Cited

U.S. PATENT DOCUMENTS

| | | |
|---|---|---|
| 2003/0050802 A1 | 3/2003 | Jay |
| 2005/0256380 A1* | 11/2005 | Nourie .................. G16H 10/60 600/300 |
| 2006/0026500 A1* | 2/2006 | Qa 'Im-maqami ... G06F 40/174 715/226 |
| 2008/0004904 A1 | 1/2008 | Tran |
| 2008/0036784 A1* | 2/2008 | Behar .................... G06Q 10/10 345/589 |
| 2012/0331567 A1* | 12/2012 | Shelton ................ G06Q 20/102 726/28 |
| 2013/0073310 A1 | 3/2013 | Awdeh |
| 2013/0173688 A1* | 7/2013 | Simpson ............ G06Q 30/0203 709/203 |
| 2013/0304493 A1 | 11/2013 | Partovi |
| 2014/0026194 A1* | 1/2014 | Smith ................. G06F 21/6245 726/4 |
| 2014/0272902 A1* | 9/2014 | Bleile ................ G06Q 30/0203 434/362 |
| 2014/0278788 A1* | 9/2014 | Du ..................... G06Q 30/0203 705/7.32 |
| 2016/0098538 A1 | 4/2016 | Dettinger |
| 2016/0267238 A1* | 9/2016 | Nag ....................... G16H 10/60 |
| 2016/0342670 A1 | 11/2016 | Smith |
| 2018/0046780 A1* | 2/2018 | Graiver ................... G06F 40/44 |

OTHER PUBLICATIONS

Sahoo, Satya S., Shiqiang Tao, Andrew Parchman, Zhihui Luo, Licong Cui, Patrick Mergler, Robert Lanese, Jill Barnholtz-Sloan, Neal J. Meropol, and Guo-Qiang Zhang. "Trial prospector: matching patients with cancer research studies using an automated and scalable approach." Cancer informatics 13 (2014) (Year: 2014).*
U.S. Appl. No. 15/677,328, filed Aug. 15, 2017 by Michelle Longmire et al for Symptom and Treatment Management Platform, 33 pages.

* cited by examiner

Research Studies

| All Fields ▷ | | | Create Study | | 🔍 Search Study Names | |
|---|---|---|---|---|---|---|
| NAME ^ | CODE | FIELD | | START DATE | END DATE | |
| Asthma Study | Asthma-1234 | Asthma, Respiratory, Lungs | | 1983-05-05 | 2019-05-05 | View |
| Migraine STudy - Complete | MIG-Finished App | Migraine, Brain, Mental Health | | 2016-05-15 | 2016-06-15 | View |

Research Studies / Create Study

Create Study Form

\* Name

The name is the study's complete name that will be seen by end-users.

Code

The code name of the study will be referenced internally by the research and development teams. Not intended to be seen by the end-users.

Description

Text to provide more information about this study.

Field

The field the study is categorized in.

Start Date  YYYY-MM-DD

End Date  YYYY-MM-DD

[Create]  [Cancel]

*FIG. 2*

Research Studies / MIG-Finished App

Edit Study Form

[ Save ] [ Cancel ]

STANDARD FIELDS

* Name: Migraine Study - Complete
The name is the study's complete name that will be seen by end-users.

Code: MIG-Finished App
The code name of the study will be referenced internally by the research and development teams. Not intended to be seen by the end-users.

Description: We are studying how and when migraines occur
Text to provide more information about this study.

Field: Migraine, Brain, Mental Health
The field the study is categorized in.

Start Date: 2016-05-15

End Date: 2016-06-15

*FIG. 3*

Research Studies / MIG-Finished App

View Study Info

[Edit Study Info]

STANDARD FIELDS

| | |
|---|---|
| *Name | Migraine Study - Complete |
| Code | MIG-Finished App |
| Description | We are studying how and when migraines occur |
| Field | Migraine, Brain, Mental Health |
| Start Date | 2016-06-15 |
| End Date | 2016-06-15 |

Tasks

[All Types ▾]    [🔍 Search Task Names]    [Create Task]

| NAME ^ | CODE | TYPE | |
|---|---|---|---|
| Consent | Consent-1234 | Consent | View |
| Eligibility | Eligibility | Eligibility | View |
| Migraine History | History-12345 | Survey | View |
| Migraine Tracker | Tracker-1 | Survey | View |

Research Studies / MIG-Finished App / Create Task

Create Task Form

* Type: [Survey ✓ / Consent / Eligibility / Predefined Active Task]

* Name: The name is the task's complete name that will be seen by end-users.

Code: The code name of the task will be referenced internally by the research and development teams. Not intended to be seen by the end-users.

Description: Text to provide more information about this study.

Start Date: YYYY-MM-DD

End Date: YYYY-MM-DD

[Create] [Cancel]

*FIG. 6*

Research Studies / MIG-Finished App / History-12345

View Task Info

[ Edit Task Info ]

STANDARD FIELDS

| | |
|---|---|
| * Name | Migraine History |
| Code | History-12345 |
| Type | Survey |
| Description | Migraine History Survey |
| Start Date | |
| End Date | |

Steps

[ Create Step ] [ Reorder Steps ] [🔍 Search Steps ]

[ All Types ▸ ]

| ORDER # | NAME | TYPE | |
|---|---|---|---|
| 1 | Introduction | Instruction | View |
| 2 | In what city do your migraines occur the most? | Location | View |
| 3 | How many migraines do you have a day? | Numeric | View |
| 4 | On average, how severe are your migraines? | Continuous Scale | View |
| 5 | What time of the day do your migraines usually happen? | Time of Day | View |
| 6 | Migraine Triggers | Text Choice | View |

*FIG. 7*

Research Studies / Migraine Study - Complete / Migraine History / Create Step Create Step Form \*Type | Step types... ▲▼

Select Step Type...

[ Cancel ]

*FIG. 8*

Research Studies / Migraine Study - Complete / Migraine History / Create Step Create Step Form

*Type ✓ Step types...
Boolean
Completion
Continuous Scale
Date/Time
Email
Image Choice
Integer Scale
Instruction
Location
Numeric
Text
Text Choice
Text Scale
Time Interval
Time of Day
Value Picker Select Step Type...

*FIG. 9*

Research Studies / Migraine Study - Complete / Migraine History / Create Step Create Step Form

**\* Type**  | Boolean ▾ |

Boolean

---

**\* Name** | |

Name for step. Mainly seen in research admin tool, not by survey participants.

**\* Text** | |

Step text, usually shown as the main question shown to the user for a step.

Description | |

Text description of step.

Optional ☐ Boolean that sets this step as optional.

[ Create ]  [ Cancel ]

*FIG. 10*

Research Studies / Migraine Study - Complete / Migraine History / Create Step Create Step Form

**\* Type**  [ Completion ▾ ]

Completion

**\* Name**  [                    ]
Name for step. Mainly seen in research admin tool, not by survey participants.

**\* Text**  [                    ]
Step text, usually shown as the main question shown to the user for a step.

Description  [                    ]
Text description of step.

Image Name  [                    ]

Optional ☐
Boolean that sets this step as optional.

[ Create ]  [ Cancel ]

*FIG. 11*

Research Studies / Migraine Study - Complete / Migraine History / Create Step

Create Step Form

| | |
|---|---|
| *Type | Continuous Scale |
| | Continuous Scale |
| *Name | |
| | Name for step. Mainly seen in research admin tool, not by survey participants. |
| *Text | |
| | Step text, usually shown as the main question shown to the user for a step. |
| Description | |
| | Text description of step. |
| Optional | ☐ |
| | Boolean that sets this step as optional. |
| Default | |
| | Number that determines default numeric value the scale starts on when the step view is loaded. |
| Fraction Digit | Integer |
| Maximum | |
| | Number that determines maximum possible numeric value that can be input by user. |
| *Maximum Description | Text |
| Minimum | |
| | Number that determines minimum possible numeric value that can be input by user. |
| *Minimum Description | Text |
| Vertical | ☐ |
| | A Boolean value indicating whether the scale is oriented vertically. |

[ Create ]  [ Cancel ]

*FIG. 12*

Research Studies / Migraine Study - Complete / Migraine History / Create Step Create Step Form

*Type [Date/Time ▾]

Date

* Name [_____]
Name for step. Mainly seen in research admin tool, not by survey participants.

* Text [_____]
Step text, usually shown as the main question shown to the user for a step.

Description
Text description of step.

Optional ☐
Boolean that sets this step as optional.

* Calendar [Gregorian]
String that determines the following: Text default - Read Only - Gregorian Default Date [YYYY-MM-DD] ☐ Add Time
Date that determines date that the datepicker starts at.

Minimum Date [YYYY-MM-DD] ☐ Add Time
Date that determines earliest date that is selectable.

Maximum Date [YYYY-MM-DD] ☐ Add Time
Date that determines latest date that is selectable.

[Create] [Cancel]

*FIG. 13*

Research Studies / Migraine Study - Complete / Migraine History / Create Step Create Step Form

**\* Type**
[Email ▾]

Email

**\* Name**
[                    ]
Name for step. Mainly seen in research admin tool, not by survey participants.

**\* Text**
[                    ]
Step text, usually shown as the main question shown to the user for a step.

Description
[                    ]
Text description of step.

Optional ☐
Boolean that sets this step as optional.

[ Create ]  [ Cancel ]

*FIG. 14*

Research Studies / Migraine Study - Complete / Migraine History / Create Step Create Step Form

* Type  [Image Choice ▾]

Image Choice

* Name  [_____]
   Name for step. Mainly seen in research admin tool, not by survey participants.

* Text  [_____]
   Step text, usually shown as the main question shown to the user for a step.

Description  [_____]
   Text description of step.

Optional  ☐
   Boolean that sets this step as optional.

Image Choices  ⋮≡
   * Image File  [Choose File] No file chosen  ☒
      Property type of File. [Create Facets of the same file, Normal Facet, Selected Facet].
   * Name  [_____]
      String
   Text  [_____]
      String - Short Text
   Value  [_____]
      String that determines the value of the image choice.

[Add New Image Choice]

[Create]  [Cancel]

*FIG. 15*

Research Studies / Migraine Study - Complete / Migraine History / Create Step Create Step Form

*Type [Instruction ◂▸]

Instruction

*Name [_____]
Name for step. Mainly seen in research admin tool, not by survey participants.

*Text [_____]
Step text, usually shown as the main question shown to the user for a step.

Description [_____]
Text description of step.

Image Name [_____]

Optional ☐ Boolean that sets this step as optional.

[Create] [Cancel]

*FIG. 16*

Research Studies / Migraine Study - Complete / Migraine History / Create Step

Create Step Form

| | |
|---|---|
| *Type | Integer Scale ◀▶ |

Integer Scale

| | | |
|---|---|---|
| *Name | [_____] | Name for step. Mainly seen in research admin tool, not by survey participants. |
| *Text | [_____] | Step text, usually shown as the main question shown to the user for a step. |
| Description | [_____] | Text description of step. |
| Optional | ☐ | Boolean that sets this step as optional. |
| Default | [_____] | Number that determines default numeric value the scale starts on when the step view is loaded. |
| Maximum | [_____] | Number that determines maximum possible numeric value that can be input by user. |
| *Maximum Description | [_____] | Text |
| Minimum | [_____] | Number that determines minimum possible numeric value that can be input by user. |
| *Minimum Description | [_____] | Text |
| Vertical | ☐ | A Boolean value indicating whether the scale is oriented vertically. |
| Step Size | [_____] | Integer number that determines the value of each step on the scale. No more than 15 steps. |

[ Create ] [ Cancel ]

*FIG. 17*

Research Studies / Migraine Study - Complete / Migraine History / Create Step Create Step Form

* Type  | Location ◀▶ |

Location

* Name  | |
Name for step. Mainly seen in research admin tool, not by survey participants.

* Text  | |
Step text, usually shown as the main question shown to the user for a step.

Description  | |
Text description of step.

Optional ☐
Boolean that sets this step as optional.

Use Current Location ☐
Boolean which determines if default starting location is set to current location.

[ Create ]  [ Cancel ]

*FIG. 18*

Research Studies / Migraine Study - Complete / Migraine History / Create Step Create Step Form Numeric

**\* Type** [ Numeric ▾ ]

**\* Name** [          ]
Name for step. Mainly seen in research admin tool, not by survey participants.

**\* Text** [          ]
Step text, usually shown as the main question shown to the user for a step.

Description [          ]
Text description of step.

Optional ☐
Boolean that sets this step as optional.

Minimum [          ]
Number that determines minimum possible numeric value that can be input by user.

Maximum [          ]
Number that determines maximum possible numeric value that can be input by user.

Style ☐
Determines whether or not the numeric step is an integer or decimal.

Unit [          ]
Text for unit the numeric step is in (years, hours, headaches, etc.).

[ Create ]  [ Cancel ]

*FIG. 19*

Research Studies / Migraine Study - Complete / Migraine History / Create Step Create Step Form \* Type  
Text Choice ◁▷

\* Name  
Name for step. Mainly seen in research admin tool, not by survey participants.

\* Text  
Step text, usually shown as the main question shown to the user for a step.

Description  
Text description of step.

Optional ☐  
Boolean that sets this step as optional.

Allow Multiples ☐  
Boolean that determines if this step allows single or multiple answers. Maps to the Style property in the Style property in the research kit.

Text Choices ≡  ☒

Display Text  
Text that displays on the choice.

\* Value  
String that determines the value of the text choice.

Exclusive ☐  
"Exclusive" property for each text choice which if true and the choice is selected, it unselects any other selected choice.

Description  
String that determines the description of the text choice. Detail Text in research kit.

[ Add New Text Choice ]

[ Create ]  [ Cancel ]

*FIG. 20*

Research Studies / Migraine Study - Complete / Migraine History / Create Step

Create Step Form

* Type [Text Scale ▾]
Text Scale

**\* Name** [_____]
Name for step. Mainly seen in research admin tool, not by survey participants.

**\* Text** [_____]
Step text, usually shown as the main question shown to the user for a step.

Description [_____]
Text description of step.

Optional ☐
Boolean that sets this step as optional.

Default Index [_____]
Number that determines starting index of the Presentation Style document array when the view is first loaded.

Vertical ☐
A Boolean value indicating whether the scale is oriented vertically.

Text Choices ⋮≡    ☒

Display Text [_____]
Text that displays on the choice.

**\* Value** [_____]
String that determines the value of the text choice.

Exclusive ☐
"Exclusive" property for each text choice which if true and the choice is selected, it unselects any other selected choice.

Description [_____]
String that determines the description of the text choice. Detail Text in research kit.

[Add New Text Choice]

[Create]    [Cancel]

*FIG. 21*

Research Studies / Migraine Study - Complete / Migraine History / Create Step Create Step Form

**\* Type**  | Text ◄► |

Text

**\* Name** | _____ |
Name for step. Mainly seen in research admin tool, not by survey participants.

**\* Text** | _____ |
Step text, usually shown as the main question shown to the user for a step.

Description | _____ |
Text description of step.

Optional ☐
Boolean that sets this step as optional.

Maximum Length | _____ |
Number that determines maximum length of text.

Multiple Lines ☑
Boolean which determines whether or not multiple lines are allowed or not.

[ Create ]  [ Cancel ]

*FIG. 22*

Research Studies / Migraine Study - Complete / Migraine History / Create Step

Create Step Form

**\* Type** | Time Interval |
Time Interval

**\* Name** | | Name for step. Mainly seen in research admin tool, not by survey participants.

**\* Text** | | Step text, usually shown as the main question shown to the user for a step.

Description | | Text description of step.

Optional ☐ Boolean that sets this step as optional.

Default Interval | | Decimal number in seconds.

Step Size | | Integer number between 1-30.

[ Create ] [ Cancel ]

*FIG. 23*

Research Studies / Migraine Study - Complete / Migraine History / Create Step Create Step Form \* Type  | Time of Day ◀▶ |

Time of Day

\* Name | |
Name for step. Mainly seen in research admin tool, not by survey participants.

\* Text | |
Step text, usually shown as the main question shown to the user for a step.

Description | |
Text description of step.

Optional ☐
Boolean that sets this step as optional.

Default Hour | |
Number determining default hour (Military).

Default Minute | |
Number determining default minute.

[ Create ]  [ Cancel ]

*FIG. 24*

Research Studies / Migraine Study - Complete / Migraine History / Create Step Create Step Form

**\* Type** [ Value Picker ⬍ ]

Value Picker

**\* Name** [_____]
Name for step. Mainly seen in research admin tool, not by survey participants.

**\* Text** [_____]
Step text, usually shown as the main question shown to the user for a step.

Description [_____]
Text description of step.

Optional [ ☐ ]
Boolean that sets this step as optional.

Text Choices ⋮⋮⋮  **\* Value** [_____]  ☒
String that determines the value of the text choice.

Description [_____]
String that determines the description of the text choice.

[ Add New Image Choice ]

[ Create ]  [ Cancel ]

*FIG. 25*

Research Studies / MIG-Finished App / History-12345 / Create Branch Rule

Create Branch Form

* Name

* Trigger Step  Introduction
The branching rule will trigger when the trigger step is completed.

* Condition  Selector Step  Introduction

Operator  Equals

Value

The condition to be evaluated when the branching rule is triggered.

* Destination Step  Introduction
The step the task will traverse to if the condition is true.

Create    Cancel

*FIG. 27*

Research Studies / MIG-Finished App / History-12345 / Create Branch Rule

Create Branch Form

**\* Name**

**\* Trigger Step** | Introduction |
The branching rule will trigger when the trigger step is completed.

**\* Condition    Selector Step** | Introduction |

Operator | ✓ Equals |
                         Not Equals
                         Less Than
            Value      Greater Than
                         Less Than or Equal To
                         Greater Than or Equal To
                         Contains
en the branching rule is triggered true.

**\* Destination Step** | Introduction |
The step the tas

[ Create ]    [ Cancel ]

*FIG. 28*

METHODS AND SYSTEMS FOR CREATING AND MANAGING A RESEARCH STUDY AND DEPLOYING VIA MOBILE AND WEB UTILIZING A RESEARCH MODULE

RELATED APPLICATION

This application, a national phase application of PCT/US2017/034335, filed May 24, 2017, which claims priority to U.S. Provisional Application No. 62/341,062 filed May 25, 2016.

BACKGROUND

Many research projects are organized as collaborations between different labs and/or institutions. In some cases, these collaborations may involve partners that are remote from each other. However, application-generating tools that are presently available may not meet the needs of researchers.

SUMMARY

The present disclosure provides methods and systems for generating a software application, such as a mobile application, that is executable by an electronic device and is configured to utilize information that is compliant under the Health Insurance Portability and Accountability Act (HIPAA).

In one aspect of the invention, a method for generating a research study application is provided. The method comprises receiving, from a user, a request to generate a research study. The method also comprises presenting, on a graphical user interface of an electronic device, a plurality of task generation options selected from the group consisting of a consent survey, an eligibility survey, a medical history survey, and a medical tracking survey.

In another aspect of the invention, a method of modifying a research study application is provided. The method comprises receiving a research study application. The method also comprises assessing the research study application for Health Insurance Portability and Accountability Act (HIPAA) compliance. Additionally, the method comprises determining that the research study application lacks a HIPAA-compliant consent survey or privacy authorization form for use or disclosure of protected health information. Further, the method comprises upon the determining, automatically updating the research study application to include a HIPAA-compliant consent survey or privacy authorization form.

In an additional aspect of the invention, a method for generating a research study application is provided. The method comprises (a) providing, to a user, a survey creation form, a task creation form, a step creation form, and a branching rule creation form. The method also comprises generating a research study application based on information received from a user in response to (a), wherein the research study application is configurable to gather information from a research study participant that interacts with the research study application.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 1 shows a screen shot of research studies, in accordance with embodiments of the invention.

FIG. 2 shows a screen shot that illustrates a blank research study creation form, in accordance with embodiments of the invention.

FIG. 3 shows a screen shot that illustrates a filled-in research study creation form, in accordance with embodiments of the invention.

FIG. 4 shows a screen shot that illustrates research study information as well as a selection of tasks, in accordance with embodiments of the invention.

FIG. 6 shows a screen shot that illustrates a task creation form that lists different available tasks, in accordance with embodiments of the invention.

FIG. 7 shows a screen shot that illustrates an exemplary survey, in accordance with embodiments of the invention.

FIG. 8 shows a screen shot that illustrates a survey step creation form, in accordance with embodiments of the invention.

FIG. 9 shows a screen shot that illustrates a survey step creation form that lists different available steps, in accordance with embodiments of the invention.

FIGS. 10-25 show screen shots that illustrate particular survey step creation forms of different available steps, in accordance with embodiments of the invention.

FIG. 26-28 shows a screen shot that illustrates a process of creating a branch rule, in accordance with embodiments of the invention.

DETAILED DESCRIPTION

Figure 5:
FIG. 5 shows a screen shot that illustrates a task creation form, in accordance with embodiments of the invention.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The ability to readily gather, access, and analyze research information is at the core of technological progress. However, there is a lack of appropriate data sharing solutions that may be used by researchers, particularly with respect to researchers who are generating data that relates to protected health information (PHI) and/or personally identifiable information (PH). In these examples, data sharing tools are needed not only to manage a research study itself, but to also share information in a way that is HIPAA-compliant. While individual researchers and/or research groups can hire software developers to create a custom application that may meet some of these requirements, there does not yet exist a research management tool that may be used to dynamically create a research management application as discussed herein.

Using the systems and methods provided herein, researchers may build their own studies without involving a software developer. By using the systems and methods provided herein to generate research studies without having to employ a software developer, researchers and research labs may be able to save money, modify research applications if/when needed, and quickly move forward with research studies by avoiding the time of finding and hiring a separate software developer.

Additionally, research applications that are able to be generated using systems and method described herein may be HIPAA-compliant. In this way, HIPAA-compliant research application may allow researchers to upload their own research data even when the data involves protected health information (PHI) and/or personally identifiable information (PH). In contrast, application-generating tools that are not HIPAA-compliant may require a researcher to rely on anonymized data or libraries of data that have already been made publicly available. However, these research-generating tools fail to provide researchers with the ability to integrate additional research data from the researchers and/or research labs themselves, which may greatly limit the progress of a particular researcher and/or research lab. Accordingly, methods and systems as provided herein may provide a great benefit to researchers by increasing the accessibility of research application-generating tools, as well as increasing the amount of data from which a researcher and/or research lab may draw from, as the methods and systems provided herein allow researchers and/or research labs to gather, analyze, and assess data that includes HIPAA-compliant data.

The present disclosure provides methods and systems for creating and managing HIPAA-compliant research applications. In examples, the research applications may be generated using a point-and-click interface. Additionally, methods are provided for dynamically generating a mobile application based on input received from a user. In examples, the dynamically generated mobile application may be provided to another party, such as a patient, a research collaborator, a doctor, or another example of a party that may be interested in the mobile application. In particular, the dynamically generated mobile application may be presented on a graphical user interface of an interested party such as a patient, research collaborator, or doctor, among other examples.

In examples, a research module may be used to interface with a HIPAA-compliant back-end as well as a research application development tool so as to allow a user to interact with both. In this way, a research module may be used with a HIPAA-compliant platform that is able to determine whether a software application, such as a mobile application, that is executable by an electronic device is compliant under the Health Insurance Portability and Accountability Act (HIPAA). Such HIPAA-compliant platforms may also include methods and systems that may automatically enable an application that is not HIPAA compliant to become HIPAA compliant.

Additionally, a research module may be used to interface with a research application development platform that provides particular user interfaces and/or structures that may be used in generating an application. However, while a previous research application development platform may require a software developer to configure a research application, a research module as discussed and described herein may facilitate a non-programmer to develop particular research applications using a user interface, such as point-and-click, in a seamless and straight-forward application. IN this way, a research module as provided herein may greatly increase the benefit of the research application development platform to the user.

FIGS. 1-28 illustrate examples of steps that a researcher may use when utilizing a research module to generate a research application as described herein.

FIG. 1 shows a screen shot of research studies, in accordance with embodiments of the invention. In particular, FIG. 1 illustrates a name for each study (e.g., "Asthma Study" and "Migraine Study—Complete"), a Code for each study (e.g., "Asthma-1234" and "MIG-Finished App). Codes may be provided for studies as researchers may refer to particular studies using a code name. FIG. 1 also illustrates a Field for each study (e.g., "Asthma, Respiratory, Lungs" and "Migraine, Brain, Mental Health"), as well as a Start Date (e.g., "1983-05-05" and "2016-05-15") and an End Date (e.g., "2019-05-05" and "2019-06-15", respectively).

A user may generate a research study using a research study creation form. Accordingly, FIG. 2 shows a screen shot that illustrates a blank research study creation form, in accordance with embodiments of the invention. The research study creation form allows users to provide information associated with the research study, such as a Name, Code, Description, Field, Start Date, and End Date. Additionally, the use of the research study creation form is straight-forward and allows the user to create the research study without having previous programming experience. Additionally, FIG. 3 shows a screen shot that illustrates a filled-in research study creation form, in accordance with embodiments of the invention. In this example, the Name of the study is "Migraine Study—Complete" and the Description is "We are studying how and when migraines occur." The additional process steps described herein relate to a migraine study, but may be associated with other types of research studies and/or other applications. In some examples, applications created may utilize gathered information, such as HIPAA-compliant research and/or medical data.

Once a research study has been created, a user may generate tasks for the research study. In examples, the user may create Consent and Eligibility tasks prior to the user providing a patient with a survey task associated with the particular study. FIG. 4 shows a screen shot that illustrates research study information as well as a selection of tasks, in accordance with embodiments of the invention. As seen in FIG. 4, an example selection of tasks include Consent, Eligibility, Migraine History survey, and Migraine Tracker survey. Additionally, each task may be of a certain type. For instance, Consent and Eligibility are a "Consent" and "Eligibility" type, respectively, whereas Migraine History and Migraine Tracker are both listed as a "Survey" type.

Initially, a user may generate a Consent survey task. In particular, prior to being involved in a research study, patients may be required to provide consent for their participation in the survey. FIG. 5 shows a screen shot that illustrates a task creation form, in accordance with embodiments of the invention. While the task creation form lists "Survey" in the task type, a user may engage a drop-down menu at the task creation form to select a task type. FIG. 6 shows a screen shot that illustrates a task creation form that lists different available tasks, in accordance with embodiments of the invention. In particular, the available tasks on the drop-down menu include "Survey," "Consent," "Eligibility," and "Predefined Activity Task." In order to generate a Consent survey, a user may select the "Consent" option.

Once a survey is created, such as a Consent survey, a user may be presented with an option of providing additional components of the survey. These components may be referred to as "steps" and the user may generate a survey by generating particular steps for a survey. FIG. 7 shows a screen shot that illustrates an exemplary survey, in accordance with embodiments of the invention. As seen in FIG. 7, steps may have different types, such as "Instruction," "Location," "Numeric," "Continuous Scale," "Time of Day," and "Text Choice," among others. An example of a survey question that is a "Location" type may be "In what city do your migraines occur the most?" An example of a survey question that is a "Numeric" type may be "How many migraines do you have a day?" An example of a survey question that is a "Continuous Scale" type may be "On average, how severe are your migraines?" An example of a survey question that is a "Time of Day" type may be "What time of day do your migraines usually happen?" An example of a survey question that is a "Test Choice" type may be "Migraine Triggers," which may be used when a user intends to generate their own survey question with associated choices.

In an additional example, a user may utilize a research module as described herein to generate an Eligibility survey. The Eligibility survey may pose questions to patients, such as whether the user has been diagnosed with a particular disease previously. For example, an Eligibility survey may be used to assess whether a patient having cancer has previously been diagnosed with cancer prior to the present occurrence. Additional questions, such as whether a patient is taking particular medications, may be used to assess whether the patient is eligible for the study and/or whether the patient is best grouped in a particular portion of the study. As such, based on the patient responses to a Consent survey and/or an Eligibility survey, the patient may continue to be eligible for the research study or the patient may become ineligible for the research study.

FIG. 8 shows a screen shot that illustrates a survey step creation form, in accordance with embodiments of the invention. A survey step creation form may be used to generate a step for a particular survey. Initially, a user may choose from a particular type of step type. FIG. 9 shows a screen shot that illustrates a survey step creation form that lists different available steps, in accordance with embodiments of the invention. In particular, FIG. 9 illustrates step types of Boolean, Completion, Continuous Scale, Date/Time, Email, Image Choice, Integer Scale, Instruction, Location, Numeric, Text, Text Choice, Text Scale, Time Interval, Time of Day, and Value Picker. In additional examples, further step types may be added.

FIGS. 10-25 show screen shots that illustrate particular survey step creation forms of different available steps, in accordance with embodiments of the invention. In particular, FIGS. 10-25 illustrate a Boolean step, Completion step, Continuous Scale step, Date/Time step, Email step, Image Choice step, Instruction step, Integer Scale step, Location step, Numeric step, Text Choice step, Text Scale step, Text step, Time Interval step, Time of Day step, and Value Picker step.

FIG. 10 shows a screen shot that illustrates a Boolean step creation form, in accordance with embodiments of the invention. An example of a Boolean step may be presenting the patient with a "Yes"/"No" question. For example, a researcher may generate a question, "Are you over 18?" which may be presented with a "Yes" or "No" answer to a patient that is taking the survey. In another example, a researcher may generate a question, "Have you previously been diagnosed with cancer?" which may be presented with a "Yes" or "No" answer to a patient taking the survey. In examples, a survey may be taken by a patient. In other examples, the survey may be taken by study participant.

FIG. 11 shows a screen shot that illustrates a Completion step creation form, in accordance with embodiments of the invention. A Completion step may be generated by a researcher to indicate that the survey has been completed. As such, a Completion step survey may be a final step in a survey. In additional examples, a Completion step may be a step that is presented to a patient prior to an Instruction step (discussed further below) that provides additional information to the patient, such as additional resources for the patient.

FIG. 12 shows a screen shot that illustrates a Continuous Scale step creation form, in accordance with embodiments of the invention. A Continuous Scale may be represented as a scale that the patient may use to indicate a feeling. The scale may have a range of, for example, 1-10 where the indication of the patient is measurable to 0.1, 0.05, or 0.01 measures between each number from 1-10. In examples, a continuous scale may be presented with a slider that the patient may engage. The slider may allow the patient to click and hold a scale engagement portion and slide the scale engagement portion to a desired response (e.g. a location on the scale associated with 8.5 on a scale of 1-10). An example of a question that may be presented to a patient includes, "How are you feeling today on a scale of 1 (bad) to 10 (excellent)?"

FIG. 13 shows a screen shot that illustrates a Date/Time step creation form, in accordance with embodiments of the invention. A Date/Time step may allow a patient to input a particular date and time when an event occurs. For example, a patient may be presented with the question, "What is the date and time of your last migraine attack?" or "What is the first time that you felt pain in your foot?" In response to the question, the patient may indicate a particular date and a particular time.

FIG. 14 shows a screen shot that illustrates an Email step creation form, in accordance with embodiments of the invention. An Email step allows a researcher to query a patient for his/her e-mail address. The patient may input his/her e-mail address into a text box.

FIG. 15 shows a screen shot that illustrates an Image Choice step creation form, in accordance with embodiments of the invention. An Image Choice step allows a researcher to present a patient with one or more images. The one or more images may be used to respond to a particular query. For example, if a patient is worried about the look of a particular mole, the researcher may provide an Image Choice that asks the patient to choose an image that most closely resembles the patient's mole. In another example, a researcher may generate a question that asks a patient to select an image that the patient can see most clearly. A patient may choose from images presented. The images that are presented may be chosen by the researcher who is designing the research study.

FIG. 16 shows a screen shot that illustrates an Instruction step creation form, in accordance with embodiments of the invention. An Instruction step may be used to present a patient with information. For example, an Instruction step may say, "Welcome to the survey" and may provide instructions for the patient.

FIG. 17 shows a screen shot that illustrates an Integer Scale step creation form, in accordance with embodiments of the invention. An Integer Scale may be similar to a Continuous Scale. An Integer Scale may provide a range of integers that a patient may choose. For example, a question may be presented to the patient, "How do you feel today on a scale of 1 (bad) to 10 (excellent)?" and the patient may be presented with a scale of 1-10 with integers 1, 2, 3, 4, 5, 6, 7, 8, 9, 10. The patient may select from the provided options.

FIG. 18 shows a screen shot that illustrates a Location step creation form, in accordance with embodiments of the invention. A Location step may be used to determine a location of a patient. In examples, the Location step may utilize a global positioning service to assess a location of a mobile device associated with the patient. In another example, the Location step may include an option for a patient to input his/her location directly. In this way, the Location step may allow a current location to be determined for the user, and/or may allow a user to enter a location of their own choosing.

FIG. 19 shows a screen shot that illustrates a Numeric step creation form, in accordance with embodiments of the invention. A Numeric step allows a researcher to generate a question that may have a numerical answer. An example of a question that may be generated during the Numeric step may ask, "How old are you?" to which a patient may input a number. Another example of a question that may be generated during the Numeric step may ask, "How many cups of coffee do you drink in a day?" to which a patient may input a number.

FIG. 20 shows a screen shot that illustrates a Text Choice step creation form, in accordance with embodiments of the invention. A Text Choice step may allow a user to generate a multiple choice question. In particular, the user/researcher may generate a question that provides two or more answers from which a user may select a choice from those provided. For example, a Text Choice question may ask, "How many cups of coffee do you drink in a day?" and may present a patient with choices, "Less than One," "One," and "Two or More." The patient may choose from these options by selecting a particular choice from those provided. In other examples, a question may ask, "Which of the following foods do you eat?" and may present a patient with choices, "Milk," "Nuts," and "Meat." In this example, the patient may choose more than one answer from the choices provided. In examples, a patient may choose one answer or more than one answer to a text choice question. In some examples, a patient may choose no answers to a text choice question.

FIG. 21 shows a screen shot that illustrates a Text Scale step creation form, in accordance with embodiments of the invention. A Text Scale may allow a researcher to ask a patient a scale-based question that has text options for answering. In particular, the user/researcher may generate a question, "How are you feeling today?" and may provide a scale with the options, "very poor," "poor," "OK," "good," or "very good." In additional examples, the user may generate a question that had different answers from which a patient may choose.

FIG. 22 shows a screen shot that illustrates a Text step creation form, in accordance with embodiments of the invention. A Text step allows a user to generate a question that a patient may answer using text. In particular, a researcher may generate a question asking, "What is your favorite color?" to which a patient may input a text response, such as "Blue" or "Purple." In another example, a user may generate a question asking, "What part of your body hurts today?" to which a patient may input a text response, such as "My feet" or "My ankle."

FIG. 23 shows a screen shot that illustrates a Time Interval step creation form, in accordance with embodiments of the invention. A Time Interval step may be used by researchers to specify a particular timeframe for answering a question. For example, a researcher may generate a question, "How long do your migraines typically last," two which a patient may respond "2 hours."

FIG. 24 shows a screen shot that illustrates a Time of Day step creation form, in accordance with embodiments of the invention. The Time of Day step may be used by researchers to generate a question that requests a response that is contextualized by a time of day. For example, a user/researcher may generate a question, "What time of day do you typically feel this way" or "What time of day do you experience a migraine," to which a patient may respond with an input of "In the morning," "10:00 pm," or a selection of a similar response that indicates a time of day. In some examples, the patient may select a particular time from a plurality of times presented to the patient.

FIG. 25 shows a screen shot that illustrates a Value Picker step creation form, in accordance with embodiments of the invention. A Value Picker step may be used by a researcher to generate a question from which a patient may select a particular value. For example, the user/researcher may generate a question, "What year were you born," and may provide a scrolling selection of years ranging from "1920" to "2015." The patient may scroll through the choices presented and may rest on a particular value.

Figure 26:
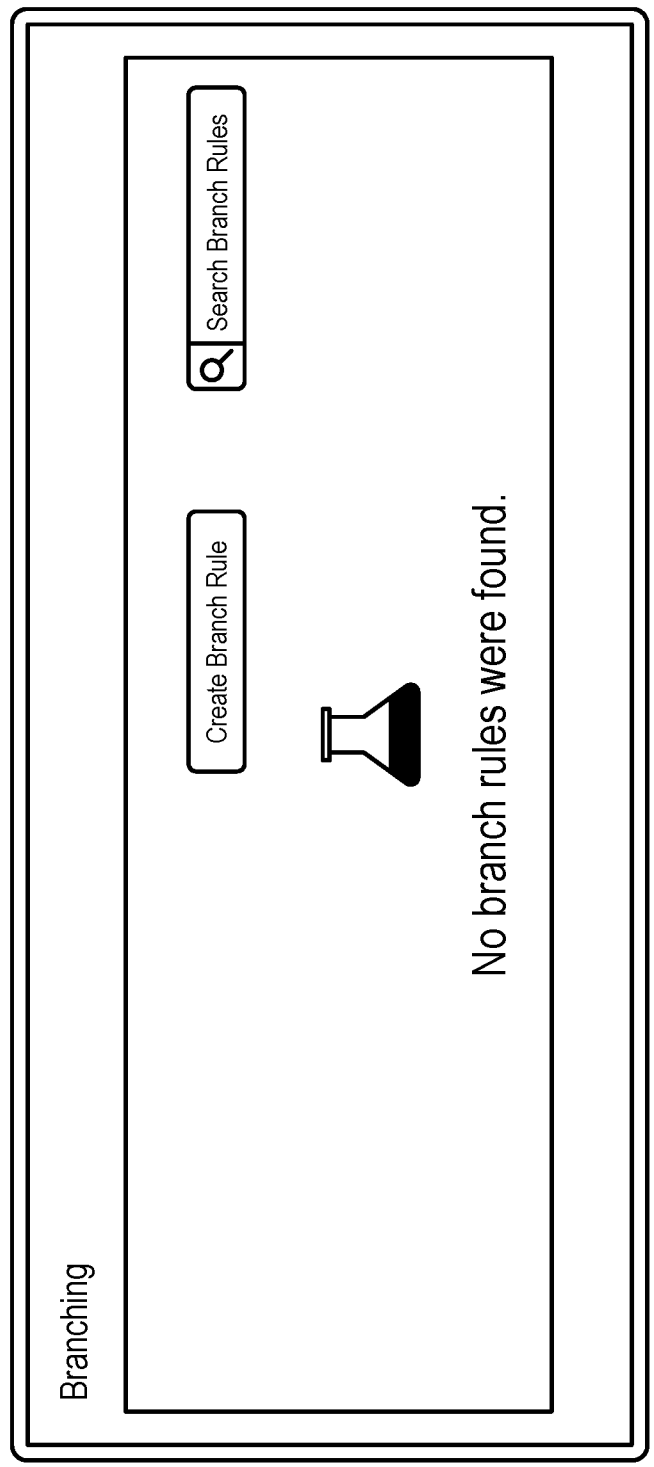

Once steps have been created, a branching rule may be created to determine an outcome of the step. For example, in an Eligibility survey, a branching rule may be used to determine whether a patient is eligible or ineligible for the research study. FIG. 26-28 shows a screen shot that illustrates a process of creating a branch rule, in accordance with embodiments of the invention.

In FIG. 26, a user is presented with existing branching rules associated with the research study. When no branching rules exist, a user is presented with an indication that no branching rules exist and is provide with an option to create a branching rule. In FIG. 27, an example of a blank form for creating a branching rule is provided. Initially, a user enters a Name to identify the branching rule.

Additionally, a user indicates a Trigger step. In particular, a Trigger step is an indication of a particular step after which a branching rule will engage once the particular step has been completed. In FIG. 27, the Trigger Step is the "Introduction." The user may also enter a Destination Step. The Destination Step may indicate the step to which the task may traverse if the condition is true. Further, the user may enter a Condition. Under the Condition portion, the user may specify a particular step (in FIG. 27, the Condition shows that the "Introduction" has been specified as the Selector Step), the user may specify an Operator, and the user may specify a value.

An Operator may be selected from a selection of Operators. In particular, FIG. 28 provides a selection of Operators such as "Equals," "Not Equals," "Less Than," "Greater Than," "Less Than or Equal To," "Greater Than or Equal To," or "Contains." While these Operators are provided as examples, additional Operators may also be used. Additionally, a Value that is entered by a user may be an outcome of the condition that is to be evaluated when the branching rule is triggered.

Once a user has generated a survey and input particular steps, the research application may be dynamically generated. In examples where a user generates branching rules, the branching rules may be assessed as a patient engages with the task. The research module may engage with additional application development platforms, such as ResearchKit on the iOS platform, in generating the research applications. In particular, the research module may pull design parameters and preferences from ResearchKit so as to allow a user to coordinate the design of a research application that is consistent with the design of that particular platform. In other examples, the The information generated by a patient when responding to a research study may be protected health information (PHI) and/or personally identifiable information (PII). As such, the research module that is used to generate the research application may be assessed using a back-end application that whether the research application generated using the research module is HIPAA-compliant. In particular, the research module may interact with a HIPAA-compliance platform that determines whether a software application, such as a mobile application, that is executable by an electronic device is compliant under the Health Insurance Portability and Accountability Act (HIPAA). In examples, a HIPAA-compliance platform may be used to assess whether particular applications is compliant with HIPAA. Such methods and systems may automatically enable an application that is not HIPAA compliant to become HIPAA compliant. Additional aspects discussed herein include data analysis characteristics, as well as integration components that allow users to make use of data analysis. Tools that may be helpful for application developers include data analysis and data integration tools.

Figure 29:
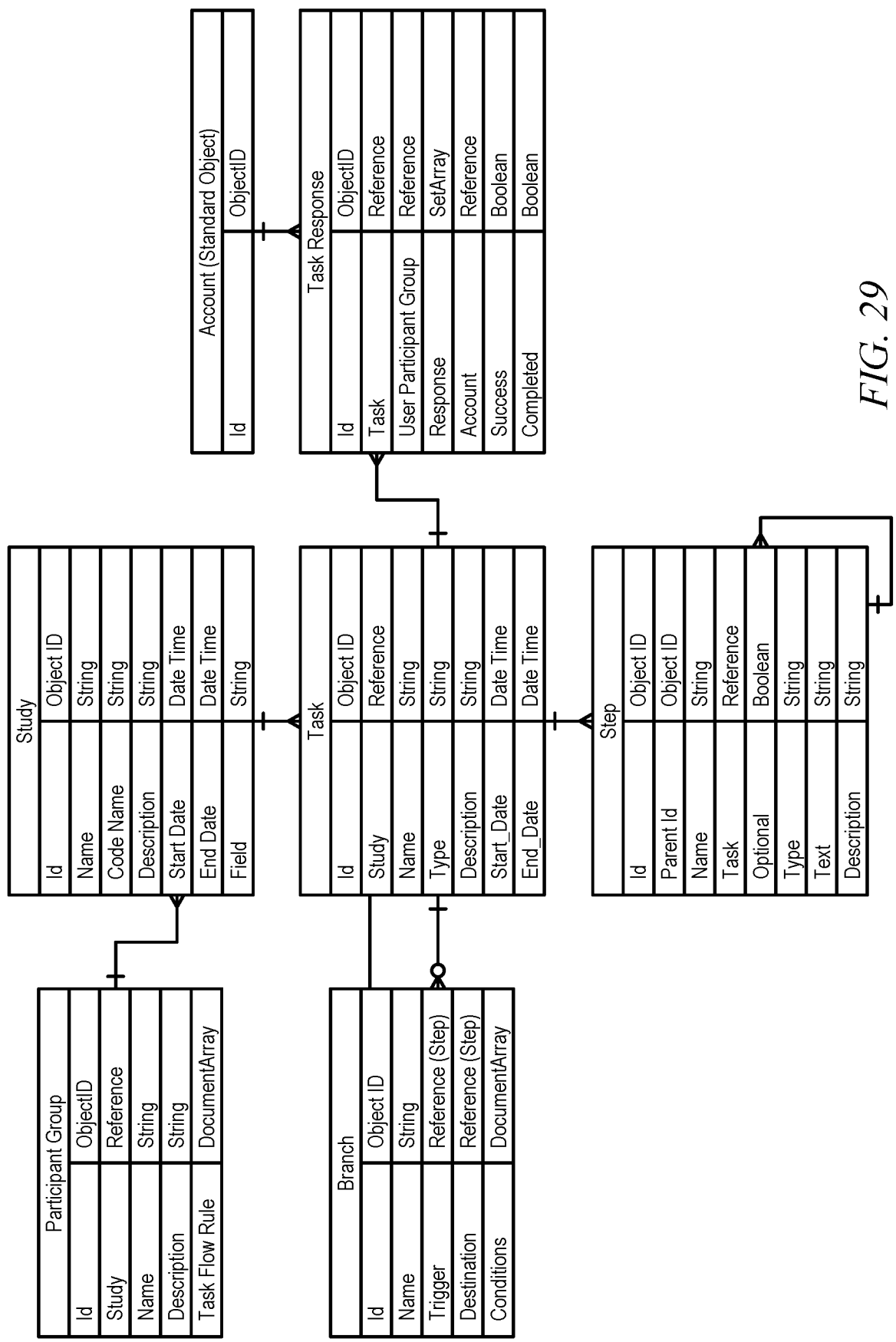
FIG. 29 illustrates a data structure for a research module, in accordance with embodiments of the invention.

FIG. 29 illustrates a data structure for a research module, in accordance with embodiments of the invention. The data structure may be used on the back-end application that may be used to integrate with a mobile client and to store the data. In particular, the data structure may be used to store the data for when a user/researcher goes through and creates records, such as creating records associated with the screen shots described herein.

Additionally, as a user generates a research study, the information gathered by and associated with the research study may be managed and/or stored within the data structure. In examples, when a researcher creates a research study, the research module that is used to generate the study may create a study object, such as seen in FIG. 29. Additionally, a study can have one or more tasks. In some examples, a study may have many tasks. In particular, a task may correlate to different kinds of tasks that can correspond with that study. In examples, tasks may leverage the mobile device of a patient that is taking a survey so as to capture data. In some examples, tasks the study participants, such as patients, may undertake tasks. In the process of undertaking tasks, data from the study participants may be captured. As such, when researchers define one or more properties of the tasks, the one or more properties may be stored as a task object as illustrated in FIG. 29.

When setting up a survey, a researcher may generate different surveys. In particular, the researcher may generate a consent survey. The consent for may be used to ensure that a potential study participant has given his/her consent to participation in the research study. In examples, the researcher may generate an eligibility survey. The eligibility survey may be used to ensure that a potential study participant is meets criteria of the research study.

Additionally, a study participant may be presented with one or more tasks that may be used to capture information from the survey participant. In examples, task may be presented separately. In examples, tasks may be combined. In examples, multiple tasks may be presented on a same screen. In examples, a task may have one step. In examples, a task may have more than one step. In examples, a task may have many steps, such as more than five steps. In examples, a task may have 1, 2, 3, 4, 5, 6, 7, 8, 9, 10, 11, 12, 13, 14, 15, 16, 17, 18, 19, 20, or more than 20 steps. In examples, a survey task may have a step such as those steps described in FIGS. 10-25 above. In examples, a survey task may be generated by a user/researcher. When tasks are generated, information associated with the tasks may be stored in a task object as seen in FIG. 29. Additionally, when steps are generated for tasks, information associated with the steps may be stored in a steps object as seen in FIG. 29.

Additionally, a user may generate branching rules. Information associated with branching rules may be stored in a branching object as seen in FIG. 29. For example, a survey may lead a study participant to different next steps based on implementation of a branching rule. The routing of one or more next steps may be stored in association with the branching rule in a branching object as seen in FIG. 29.

FIG. 29 also illustrates a participant group table. In examples, study participants who become enrolled in a research study may fall into different categories/groups in the study. For examples, some participants may be categorized in a control group while some patients may be randomized. Additional groups may also be created based on defining parameters of a participant group. This information may be stored in a participant group object.

Further, when study participants and/or potential study participants respond to a task, the task response may be stored in a task response object, as seen in FIG. 29. In examples, data that is captured through a mobile application may go to the task response table. The data that is captured by the mobile device may include information in addition to the participant's input response. For example, additional information that may be collected may include a time of day that a participant is responding to the question. Additionally, responses that are received from study participants may be associated with the participant's account. In examples, account information may be stored in an Account object.

Computer Control Systems

Figure 30:
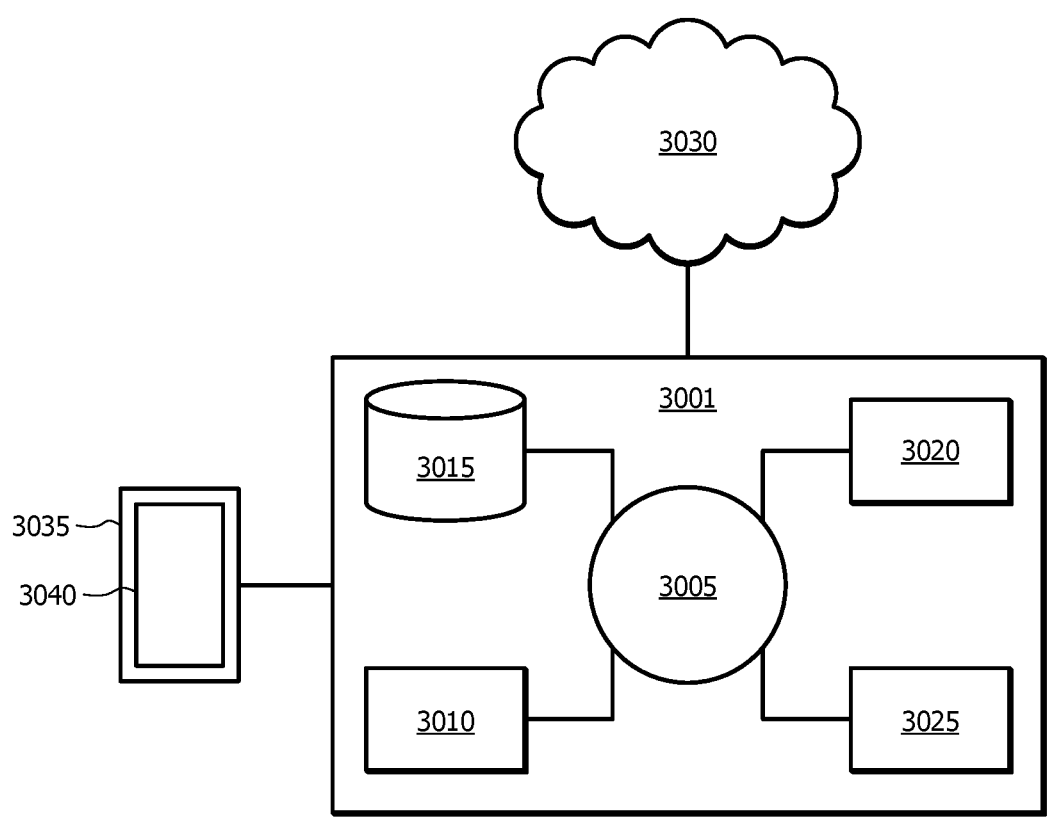
FIG. 30 shows a computer control system that is programmed or otherwise configured to implement methods provided herein.

The present disclosure provides computer control systems that are programmed to implement methods of the disclosure. FIG. 30 shows a computer system 3001 that is programmed or otherwise configured to create research surveys; manage research surveys; create HIPAA-compliant applications; and/or dynamically represent generated research surveys in a mobile application for users to use. The computer system 3001 includes a central processing unit (CPU, also "processor" and "computer processor" herein) 3005, which can be a single core or multi core processor, or a plurality of processors for parallel processing. The computer system 3001 also includes memory or memory location 3010 (e.g., random-access memory, read-only memory, flash memory), electronic storage unit 815 (e.g., hard disk), communication interface 3020 (e.g., network adapter) for communicating with one or more other systems, and peripheral devices 3025, such as cache, other memory, data storage and/or electronic display adapters. The memory 3010, storage unit 3015, interface 3020 and peripheral devices 3025 are in communication with the CPU 3005 through a communication bus (solid lines), such as a motherboard. The storage unit 3015 can be a data storage unit (or data repository) for storing data. The computer system 3001 can be operatively coupled to a computer network ("network") 3030 with the aid of the communication interface 3020. The network 3030 can be the Internet, an internet and/or extranet, or an intranet and/or extranet that is in communication with the Internet. The network 3030 in some cases is a telecommunication and/or data network. The network 3030 can include one or more computer servers, which can enable distributed computing, such as cloud computing. The network 3030, in some cases with the aid of the computer system 3001, can implement a peer-to-peer network, which may enable devices coupled to the computer system 3001 to behave as a client or a server.

The CPU 3005 can execute a sequence of machine-readable instructions, which can be embodied in a program or software. The instructions may be stored in a memory location, such as the memory 3010. The instructions can be directed to the CPU 3005, which can subsequently program or otherwise configure the CPU 3005 to implement methods of the present disclosure. Examples of operations performed by the CPU 3005 can include fetch, decode, execute, and writeback.

The CPU 3005 can be part of a circuit, such as an integrated circuit. One or more other components of the system 3001 can be included in the circuit. In some cases, the circuit is an application specific integrated circuit (ASIC).

The storage unit 3015 can store files, such as drivers, libraries and saved programs. The storage unit 3015 can store user data, e.g., user preferences and user programs. The computer system 3001 in some cases can include one or more additional data storage units that are external to the computer system 3001, such as located on a remote server that is in communication with the computer system 3001 through an intranet or the Internet.

The computer system 3001 can communicate with one or more remote computer systems through the network 3030. For instance, the computer system 3001 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 3001 via the network 3030.

Methods as described herein can be implemented by way of machine (e.g., computer processor) executable code stored on an electronic storage location of the computer system 3001, such as, for example, on the memory 3010 or electronic storage unit 3015. The machine executable or machine readable code can be provided in the form of software. During use, the code can be executed by the processor 3005. In some cases, the code can be retrieved from the storage unit 3015 and stored on the memory 3010 for ready access by the processor 3005. In some situations, the electronic storage unit 3015 can be precluded, and machine-executable instructions are stored on memory 3010.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 3001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 3001 can include or be in communication with an electronic display 3035 that comprises a user interface (UI) 3040. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 3005. The algorithm can, for example, determine whether an application is HIPAA compliant.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for generating a research study application for a research study, the method comprising:
    presenting, on a display screen, one or more graphical user interfaces;
    receiving, via the one or more graphical user interfaces, research study commands defining a type of the research study application, wherein a plurality of different research study commands define a plurality of different types of research study applications;
    receiving, via the one or more graphical user interfaces, consent commands for a consent task, wherein the consent commands define patient consent parameters for the research study application;
    receiving, via the one or more graphical user interfaces, eligibility commands for an eligibility task, wherein the eligibility commands define patient eligibility parameters for the research study application;
    receiving, via the one or more graphical user interfaces, one or more rule commands of a rule for at least one of the consent task and an eligibility task, wherein the rule commands define a trigger for engaging the rule and a condition for evaluating patient input
    generating the research study application, wherein the research study application is of the type of plurality of different types of research study application, and where the research study application includes (1) a consent portion that requires patient consent input for the patient consent parameters, and (2) an eligibility portion that requires patient eligibility input for the patient eligibility parameters;
    transmitting the generated search study application to a plurality of patient devices associated with a plurality of patients participating in the research study, the plurality of patient devices executing the research study application that executes at least one of the consent task or the eligibility task;
    receiving, from at least one patient device associated with at least one patient, at least one of patient consent input from the consent portion or patient eligibility input for the eligibility portion; and
    determining at least one of (1) patient consent for the research study based on the rule commands, the patient consent input, and the patient consent parameters, or (2) patient eligibility for the research study based on the rule commands, the patient eligibility input, and the patient eligibility parameters.

2. The method of claim 1, further comprising:
    receiving, via the one or more graphical user interfaces, survey commands that define one or more surveys with questions related to the type of the research study application, wherein the research study application includes one or more survey portions that require patient survey input for the one or more surveys; and
    receiving, via the one or more graphical user interfaces, a selection of a step type to define a particular survey of the one or more surveys, wherein the step type is one of a Boolean step type, a Completion step type, a Continuous Scale step type, a Date/Time step type, an Email step type, an Image Choice step type, an Integer Scale step type, an Instruction step type, a Location step type, a Numeric step type, a Text step type, a Text Choice step type, a Text Scale step type, a Time Interval step type, a Time of Day step type, and a Value Picker step type.

3. The method of claim 2, wherein the selection of the Boolean step type generates a user query and a first and second answer for the user query when the research study application executes on a patient computing device.

4. The method of claim 2, wherein the selection of the Completion step type generates an indication, configured to be displayed on a patient computing device, that the particular survey of the research study application is completed when the research study application executes on the patient computing device.

5. The method of claim 2, wherein the selection of the Continuous Scale step type generates (1) a user query when the research study application executes on a patient computing device, and (2) a graphical scale from a beginning value to an ending value, wherein the graphical scale is configured to be adjusted between and including the beginning value and the ending value when the research study application executes on the patient computing device.

6. The method of claim 2, wherein the selection of the Date/Time step type generates a user query and a Date and/or Time graphic that is configured to be adjusted to any date and/or time when the research study application executes on a patient computing device.

7. The method of claim 2, wherein the selection of the Email step type generates an e-mail input box that is configured receive a valid email address when the research study application executes on a patient computing device.

8. The method of claim 2, wherein the selection of the Image step type generates a user query and one or more images that are associated with one or more proposed responses to the user query when the research study application executes on a patient computing device.

9. The method of claim 2, wherein the selection of the Location step type generates, when the research study application executes on a patient computing device, a user query and determines a user location in response to a particular response to the user query received on patient computing device, wherein the user location is determined based on at least one of a global positioning service or received user location input.

10. The method of claim 2, wherein the selection of the Integer Scale step type generates a user query and a plurality of selectable integers to respond to the user query when the research study application executes on a patient computing device.

11. The method of claim 2, wherein the selection of the Instruction step type generates one or more instructions to be performed by a patient when the research study application executes on a patient computing device.

12. The method of claim 2, wherein the selection of the Numeric step type generates a user query and a number input box configured to receive a numerical value for a response to the user query when the research study application executes on a patient computing device.

13. The method of claim 2, wherein the selection of the Text Choice step type generates a user query and two or more proposed, text-based responses for responding to the user query when the research study application executes on a patient computing device.

14. The method of claim 2, wherein the selection of the Text Scale step type generates a user query and a scale with selected text-based options for responding to the user query when the research study application executes on a patient computing device.

15. The method of claim 2, wherein the selection of the Time Interval step type generates a user query and a length of time input box configured to receive a length of time for responding to the user query when the research study application executes on a patient computing device.

16. The method of claim 2, wherein the selection of the Value Picker step type generates a user query and a plurality of graphical values that are selectable for responding to the user query when the research study application executes on a patient computing device.

17. The method of claim 2, wherein the research study application is one of a mobile application, a web-based application, and a Health Insurance Portability and Accountability Act (HIPAA)-compliant application that is accessible via a patient computing device.

18. A system for generating a research study application for a research study, the system comprising:
a processor coupled to a memory, the processor configured to:
present, on a display screen, one or more graphical user interfaces;
receive, via the one or more graphical user interfaces, research study commands defining a type of the research study application, wherein a plurality of different research study commands define a plurality of different types of research study applications;
receive, via the one or more graphical user interfaces, consent commands for a consent task, wherein the consent commands define patient consent parameters for the research study application; and
receive, via the one or more graphical user interfaces, eligibility commands for an eligibility task, wherein the eligibility commands define patient eligibility parameters for the research study application;
receive, via the one or more graphical user interfaces, one or more rule commands of a rule for at least one of the consent task and the eligibility task, wherein the rule commands define a trigger for engaging the rule and a condition for evaluating patient input;
generate the research study application, wherein the research study application includes (1) a consent portion that requires patient consent input for the patient consent parameters, and (2) an eligibility portion that requires patient eligibility input for the patient eligibility parameters;
transmit the generated search study application to a plurality of patient devices associated with a plurality of patients participating in the research study, the plurality of patient devices executing the research study application that executes at least one of the consent task or the eligibility task;
receive, from at least one patient device associated with at least one patient, at least one of patient consent input from the consent portion or patient eligibility input for the eligibility portion; and
determine at least (1) patient consent for the research study based on the rule commands, the patient consent input, and the patient consent parameters, or (2) patient eligibility for the research study based on the rule commands, the patient eligibility input, and the patient eligibility parameters.

19. The system of claim 18, the processor further configured to:
receive, via the one or more graphical user interfaces, survey commands that define one or more surveys with questions related to the type of the research study application, wherein the research study application includes one or more survey portions that require patient survey input for the one or more surveys; and
receive, via the one or more graphical user interfaces, a selection of a step type to define a particular survey of the one or more surveys, wherein the step type is one of a Boolean step type, a Completion step type, a Continuous Scale step type, a Date/Time step type, an Email step type, an Image Choice step type, an Integer Scale step type, an Instruction step type, a Location step type, a Numeric step type, a Text step type, a Text Choice step type, a Text Scale step type, a Time Interval step type, a Time of Day step type, and a Value Picker step type.

20. A non-transitory computer-readable medium including program instruction that when executed cause a processor to:
present, on a display screen, one or more graphical user interfaces;
receive, via the one or more graphical user interfaces, research study commands defining a type of a research study application, wherein a plurality of different research study commands define a plurality of different types of research study applications;
receive, via the one or more graphical user interfaces, consent commands for a consent task, wherein the consent commands define patient consent parameters for the research study application; and
receive, via the one or more graphical user interfaces, eligibility commands for an eligibility task, wherein the eligibility commands define patient eligibility parameters for the research study application;
receive, via the one or more graphical user interfaces, one or more rule commands of a rule for at least one of the consent task and the eligibility task, wherein the rule commands define a trigger for engaging the rule and a condition for evaluating patient input;
generate the research study application, wherein the research study application includes (1) a consent portion that requires patient consent input for the patient consent parameters, and (2) an eligibility portion that requires patient eligibility input for the patient eligibility parameters;
transmit the generated search study application to a plurality of patient devices associated with a plurality of patients participating in the research study, the plurality of patient devices executing the research study application that executes at least one of the consent task or the eligibility task;

receive, from at least one patient device associated with at least one patient, at least one of patient consent input from the consent portion or patient eligibility input for the eligibility portion; and determine at least (1) patient consent for the research study based on the rule commands, the patient consent input, and the patient consent parameters, or (2) patient eligibility for the research study based on the rule commands, the patient eligibility input, and the patient eligibility parameters.

\* \* \* \* \*